United States Patent [19]

Khanna

[11] Patent Number: 4,992,278

[45] Date of Patent: Feb. 12, 1991

[54] THERAPEUTIC SYSTEM FOR SPARINGLY SOLUBLE ACTIVE INGREDIENTS

[75] Inventor: Satish C. Khanna, Bottmingen, Switzerland

[73] Assignee: Ciba-Geigy Corporation, Ardsley, N.Y.

[21] Appl. No.: 390,435

[22] Filed: Aug. 3, 1989

Related U.S. Application Data

[63] Continuation of Ser. No. 140,467, Jan. 4, 1988, abandoned.

[30] Foreign Application Priority Data

Jan. 14, 1987 [CH] Switzerland .............................. 116/87

[51] Int. Cl.$^5$ ................................................ A61K 9/24
[52] U.S. Cl. ..................................... 424/473; 424/468; 424/469
[58] Field of Search ............... 424/464, 468, 472, 473, 424/467, 470

[56] References Cited

U.S. PATENT DOCUMENTS

| | | | |
|---|---|---|---|
| 3,845,770 | 11/1974 | Theeuwes et al. ................... | 128/260 |
| 4,060,598 | 11/1977 | Groppenbacher et al. ........ | 424/482 |
| 4,111,202 | 9/1978 | Theeuwes ........................... | 128/260 |
| 4,327,725 | 5/1982 | Cortese et al. ...................... | 128/260 |
| 4,624,847 | 11/1986 | Ayer et al. ........................... | 424/467 |
| 4,685,918 | 8/1987 | Amidon et al. ..................... | 604/892 |
| 4,692,336 | 9/1987 | Eckenhoff et al. ................. | 424/487 |

FOREIGN PATENT DOCUMENTS 1560406  2/1980  United Kingdom .
2150830  7/1985  United Kingdom .

OTHER PUBLICATIONS

Theeuwes, J. Pharm. Sc., vol. 64, No. 12, pp. 1987–1991 (1975).

Primary Examiner—Thurman K. Page
Assistant Examiner—Leon R. Horne
Attorney, Agent, or Firm—JoAnn Villamizar

[57]  ABSTRACT

The present invention relates to a therapeutic system with systemic action for peroral administration, having a compartment for active ingredients, which system contains in that compartment sparingly soluble active ingredients, swelling agents and, optionally, water-soluble substances for producing an osmotic pressure.

7 Claims, No Drawings

THERAPEUTIC SYSTEM FOR SPARINGLY SOLUBLE ACTIVE INGREDIENTS

This application is a continuation of application Ser. No. 140,467, filed Jan. 4, 1988, now abandoned.

The present invention relates to a therapeutic system with systemic action for oral administration, having a compartment for active ingredients, which system contains in that compartment sparingly soluble active ingredients, swelling agents and, optionally, water-soluble substances for producing an osmotic pressure, and to processes for the manufacture of such a system.

Therapeutic systems for obtaining a systemic action are known. In the case of the peroral system OROS ®: Oral Osmotic System (Alza Corp.), which is described by F. Theeuwes in J. Pharm. Sc. Vol. 64, 12, 1987-1991 (1975) and in its simplest version takes the form of a conventional coated tablet, aqueous body fluids pass continuously through the outer layer, which acts as a semi-permeable membrane, into the system, reach the active ingredient present in solid form in the core, and dissolve it. If the active ingredient is sufficiently soluble in water, the active ingredient-containing solution is released at a constant rate through an outlet opening approximately 100-250 micrometers wide as a result of the osmotic pressure that builds up.

This form of administration achieves an adequate release rate for the active ingredient, and hence the desired therapeutic effect, if the active ingredient in the core is able to produce a sufficiently high osmotic pressure. A precondition for this is a sufficiently high content of water-soluble active ingredient with a correspondingly low proportion of adjuncts in the core.

For that reason the OROS ® systems are not suitable for sparingly soluble active ingredients. Especially in the case of active ingredients that are administrable in high doses, such as carbamazepine, the osmotic pressure would be too low. In order to solve this problem, U.S. Pat. No. 4,111,202 describes double-compartment systems for sparingly soluble active ingredients ("push-pull" systems) which contain the active ingredient or active ingredient formulation in one compartment and in a compartment below it water-soluble compounds for producing an osmotic pressure, for example salts or sugars. The two compartments are separated from one another by a flexible wall and are sealed towards the outside by means of a rigid but water-permeable semi-permeable membrane. On the admission of water the osmotic pressure that builds up increases the volume of the lower compartment. Because the semi-permeable wall is rigid, the osmotic pressure acts on the flexible partition wall which expands during the process and forces the contents of the compartment containing the active ingredient out of the system.

The manufacture of "push-pull" systems is technically complicated, since a flexible partition wall made of a different material from the semi-permeable casing has to be incorporated in such forms of administration. In addition, in the case of sparingly soluble and high-dosage active ingredients, such as, for example, carbamazepine, with a dosage of, for example, more than 200 mg, it is only possible to make large "push-pull" systems, which can be difficult for the patient to take.

European Patent Application No. 52917 describes compartment systems for sparingly soluble active ingredients without a partition wall. The osmotic propellant is contained in the active ingredient compartment. The compartment below it consists of swellable polymers, such as polyvinylpyrrolidone. The osmotic pressure that builds up brings about an increase in the liquid uptake of the system, which accelerates the swelling. The swelling pressure increases the volume only of the compartment consisting of swellable polymers and, because the semi-permeable wall is rigid, forces the contents of the active ingredient compartment out through an opening.

The form of administration described in European Patent Application No. 52917 can be regarded as a two-layer tablet having a casing or coating. Its manufacture is technically complicated compared with that of simple encased or coated tablets. For example, the compression operation has to be carried out in at least two stages. In the customary compression of different granulates there are stringent requirements as regards the uniformity of the grains of the granulate components that are compressed together. Reference is made to the description of the manufacture of multi-layered tablets, the technical problems involved and the requirements regarding the granulates used, in Hager's Handbuch der Pharmazeutischen Praxis, Springer Verlag 1971, in the subsequent "Hager", Volume VIIa, bottom of page 710 and bottom of page 723 to page 725.

The problem underlying the present invention is to manufacture oral therapeutic systems for sparingly soluble active ingredients having only one compartment, the size of which is to be kept so small that it corresponds to the oral osmotic systems for soluble active ingredients known hitherto.

This problem is solved by selecting an advantageous swelling agent which is suitable for the manufacture of single-compartment systems and provides the single-compartment system with an adequate release capacity. Known swelling agents, such as polyvinylpyrrolidone, polyethylene oxide, polymethacrylate, etc., are disadvantageous in single-compartment systems, since the swelling pressure is so great that in contact with water the semi-permeable membrane bursts and the whole system disintegrates in the stomach after a short time.

The invention relates to a therapeutic system with systemic action for peroral administration in the form of a coated or encased single-compartment system for the administration of active ingredients that are sparingly soluble in water and may need to be administered in high doses.

The therapeutic system according to the invention comprises:

(a) a casing made of a material that is permeable to water and is impermeable to the components of the core containing the active ingredient, (b) a core containing an active ingredient that is sparingly soluble in water or a mixture of such active ingredients, a hydrophilic, polymeric swelling agent consisting of a mixture of a vinylpyrrolidone/vinyl acetate copolymer with an ethylene oxide homopolymer, optionally a water-soluble substance for inducing osmosis and, optionally, further pharmaceutically acceptable adjuncts and (c) a passage through the casing (a) for the transport of the constituents contained in the core into the surrounding aqueous body fluid.

The definitions and terms used hereinbefore and hereinafter preferably have the following meanings in the context of the description of the present invention:

The casing (a) made of a material that is permeable to water and impermeable to the components of the core containing the active ingredient can be in the form of a semi-permeable membrane which is permeable to water but is impermeable to the constituents contained in the core of the form of administration, such as active ingredients, swelling agents, adjuncts etc.

The polymeric substances described in the literature, for example in U.S. Pat. Nos. 3,916,899 and 3,977,404, which are not metabolished in the gastro-intestinal tract, that is to say are excreted unchanged, are suitable for the manufacture of the casing made of semi-permeable material. For example, it is possible to use acylated cellulose derivatives (cellulose esters) that are mono-to tri-substituted by acetyl groups or mono- or di-substituted by acetyl groups and substituted by a further acyl radical other than acetyl, for example cellulose acetate, cellulose triacetate, agar acetate, amylose acetate, cellulose acetate ethyl carbamate, cellulose acetate phthalate, cellulose acetate methyl carbamate, cellulose acetate succinate, cellulose acetate dimethylaminoacetate, cellulose acetate ethyl carbonate, cellulose acetate chloroacetate, cellulose acetate ethyl oxalate, cellulose acetate methyl sulphonate, cellulose acetate butyl sulphonate, cellulose acetate propionate, cellulose acetate diethylamino-acetate, cellulose acetate octate, cellulose acetate laurate, cellulose acetate p-toluenesulphonate, cellulose acetate butyrate and other cellulose acetate derivatives. Also suitable as semi-permeable membrane material are hydroxypropylmethyl-cellulose and polymeric epoxides, copolymers of alkylene oxides and alkyl glycidyl ethers, polyglycols or polylactic acid derivatives and further derivatives thereof. It is also possible to use mixtures, such as, for example, of acrylates that are insoluble in water per se (for example the copolymer of acrylic acid ethyl ester and methacrylic acid methyl ester).

The active ingredient contained in the core of the therapeutic system according to the invention is sparingly soluble in water, and especially in body fluids such as gastric or intestinal juices, and is therefore not easily resorbed. When using conventional peroral forms of administration, such as dragées or tablets, a high dosage is usually required which puts a corresponding strain on the mucous membranes in the stomach when administered at intervals. For example, the commercially available preparations containing acetyl-salicylic acid contain up to 500 mg of active ingredient per tablet.

Suitable active ingredients for the therapeutic system according to the invention preferably have a solubility of less than 5 g in 100 ml of water at 37° C. and are selected from various groups of indication, for example from the group comprising the hypnotics/sedatives, psychopharmacological agents, antihypertensives, muscle relaxants, analgesics and/or anti-inflammatory drugs, spasmolytics, agents for gastritis and/or ulceration, anticonvulsants, diuretics, etc.

Unless otherwise indicated, the names used for the active ingredients mentioned in the description of the invention are the World Health Organisation (WHO) Recommended International Non-Proprietary Names (INN names) taken from the "Rote Liste" (Red List), the updated edition of which appears annually (published by: Bundesverband der Deutschen Pharmazeutischen Industrie, D-6000 Frankfurt a.M.), and the Merck Index (Tenth Edition).

Especially suitable active ingredients are hypnotics/sedatives, such as azacyclonol or buclizine; psychopharmacological agents, such as diazepam, chlordiazepoxide, oxazepam, oxanamide, hydroxyphenamate, phenaglycodol, haloperidol, perphenazine, thiothixene etc.; anti-hypertensives, such as mebutamate; anti-epileptic agents, such as diphenylhydantoin, metharbital, methsuximide, paramethadione, phensuximide, primidone, trimethadione or carbamazepine; analgesics and/or anti-inflammatory agents, for example acetaminophen, acetyl-salicylic acid, etc.; CNS stimulants, for example bronchiospasmolysants, such as theophylline; calcium antagonists, such as nifedipine or nicardipine; antibacterial agents, such as nitrofurantoin, idoxuridine; penicillins, such as ampicillin; cephalosporins, such as cefaclor, cephalexin, cefsulodin or cefotiam, and so on.

It is also possible for the therapeutic system according to the invention to contain the customary mixtures of the mentioned active ingredients and their analogues, which are not mentioned here.

For the therapeutic system according to the invention the active ingredients are used in finely particulate form. The expression "finely particulate form" includes micronised, amorphous anhydrous and crystalline anhydrous forms and crystalline hydrate forms. Micronised crystalline anhydrous forms are preferred. The particle size must be small enough to ensure free-flowing release of the active ingredient through the opening in the semi-permeable membrane, which opening has a preferred diameter of approximately 0.4-0.8 mm. In addition, with a small particle size there is improved resorption of dispersed particles of the sparingly soluble active ingredients. In a preferred embodiment, anhydrous crystals of active ingredients having a particle size smaller than 100 μm, especially smaller than 20 μm, are used. Details of dosages can be found in the PDR (Physicians' Desk Reference, Medical Economics Co.).

The hydrophilic swelling agent contained in the core (b) is a polymer which interacts with water from the aqueous body fluid contained in the gastro-intestinal tract, swells and is able to expand until it reaches a state of equilibrium. The swelling agent is capable of absorbing large quantities of water and of producing the swelling pressure required for the therapeutic system to function.

The hydrophilic, polymeric swelling agent used in the therapeutic system according to the invention consists of a mixture of a vinylpyrrolidone/vinyl acetate copolymer and an ethylene oxide homopolymer. This mixture has the surprising advantage that the pressure produced during swelling does not lead to rupturing of the system and the swelling speed is uniform so that almost constant amounts of active ingredient are released from the system. The vinylpyrrolidone/vinyl acetate copolymer component preferably has a molecular weight of 60,000±15,000. The ratio of the monomers vinylpyrrolidone and vinyl acetate which form the basis of the copolymer is preferably approximately 60:40 (% by weight). The vinylpyrrolidone/vinyl acetate copolymer has the following properties:

purity: 95% (remainder water), insoluble in ether, aliphatic hydrocarbons, readily soluble in water, ethyl and isopropyl alcohol, methylene chloride, glycerin and 1,2-propylene glycol, pH value of a 10% aqueous solution 3–5, viscosity (10% aqueous solution): 5 mPas, see H. P. Fiedler, Lexikon der Hilfsstoffe, H. P. Fiedler, Editio Cantor 1982.

Vinylpyrrolidone/vinyl acetate copolymers are known and/or can be manufactured in a manner known per se with any desired mixing ratio of the monomers. The preferred 60:40 copolymer is commercially available, for example, under the trade name Kollidon ® VA 64 (BASF).

The vinylpyrrolidone/vinyl acetate copolymer is mixed with an ethylene oxide homopolymer having a degree of polymerisation of approximately $2.0 \times 10^3 - 1.0 \times 10^5$ and a corresponding approximate molecular weight of approximately $1.0 \times 10^5 - 5.0 \times 10^6$ and having the following properties:

for a molar weight of approximately 4,000 and above solid wax-like substances. Miscible in any ratio with water and each other. Soluble in methanol, ethanol, acetone, methylene chloride.

Ethylene oxide homopolymers (polyethylene glycols) are known and are commercially available in various degrees of polymerisation, for example under the name Polyox ® (Union Carbide). It is preferable to use Polyox ® (coagulant) having a molecular weight of more than $1.0 \times 10^6$.

In a preferred embodiment of the invention a 1:1 mixture (by weight) of vinylpyrrolidone/vinyl acetate copolymer (commercial form: Kollidon ® VA 64) and ethylene oxide homopolymer (commercial form Polyox ® MW: $5 \times 10^6$) is used.

The hydrophilic, polymeric swelling agent can be present in the core in parts by weight of approximately 5–60%, based on the total weight of the therapeutic system in question.

Due to the prevailing concentration gradient, once water has penetrated the semi-permeable casing, the water-soluble substances for inducing osmosis that are optionally contained in the core in addition to the swelling agents produce an osmotic pressure and reinforce the swelling pressure. Since the semi-permeable casing (a) is rigid or at least only slightly elastic, the pressure produced by osmosis and swelling can be balanced only by release of the material contained in the core through the passage (c) in the membrane.

Water-soluble substances that are suitable for inducing osmosis are in principle all water-soluble substances acceptable for use in pharmacy, for example the water-soluble adjuncts mentioned in pharmacopoeias or in "Hager" as well as in Remington's Pharmaceutical Science. Especially suitable are pharmaceutically acceptable water-soluble salts of inorganic or organic acids or non-ionic organic substances having an especially high degree of solubility in water, for example carbohydrates, such as sugar, or amino acids, for example glycine.

Such water-soluble substances for inducing osmosis are, for example, inorganic salts, such as magnesium chloride or sulphate, lithium, sodium or potassium chloride, lithium, sodium or potassium sulphate or sodium or potassium hydrogen phosphate or dihydrogen phosphate, salts of organic acids, such as sodium or potassium acetate, magnesium succinate, sodium benzoate, sodium citrate or sodium ascorbate, carbohydrates, such as arabinose, ribose or xylose (pentoses), glucose, fructose, galactose or mannose (hexoses), sucrose, maltose or lactose (disaccharides) or raffinose (trisaccharides), water-soluble amino acids, such as glycine, leucine, alanine or methionine, urea etc., and mixtures thereof. These water-soluble adjuncts can be present in the core in parts by weight of approximately 0.01–35%, based on the total weight of the therapeutic system in question.

In addition to the water-soluble substances for inducing osmosis and the hydrophilic polymeric swelling agent, the core (b) can contain further pharmaceutically acceptable adjuncts. Such adjuncts are, for example, protective colloids, which inhibit any potential crystal growth of active ingredients in water and prevent the formation of relatively large hydrate crystals from finely particulate particles. Above all, protective colloids can prevent the formation of relatively large hydrate crystals from anhydrous modifications or amorphous particles. As mentioned hereinbefore, the formation of relatively large crystals impairs the continuous release capacity of the therapeutic system (blockage of the passage through which the active ingredient is transported out of the system and prevention of the release of the active ingredient).

Suitable protective colloids are especially methylated cellulose derivatives, for example methyl cellulose having a methoxy content of approximately from 27.0 to 32.0% and a degree of substitution of approximately from 1.75 to 2.1, or methylhydroxypropylcellulose having a content of approximately 16.0–30.0% methoxy and 4.0–32.0% hydroxypropoxy groups. Protective colloids, such as methylhydroxypropylcellulose, can be present in the therapeutic system according to the invention in a preferred ratio of approximately 0.5–10%, based on the amount of active ingredient.

For example, the addition of this protective colloid prevents or retards the growth, observed in the aqueous phase, of anhydrous carbamazepine microcrystals up to 100 μm, especially 1–20 μm, in size or hydrates thereof of similar size to form needle-like hydrates approximately 100–500 μm in size.

The therapeutic system according to the invention is able to release microcrystals having an average size of approximately 1–20 μm into the gastro-intestinal tract. Active ingredients can therefore be dissolved more rapidly in especially finely dispersed form.

Further adjuncts are, for example, plasticisers, which improve the flow properties and the handling of the hydrophilic polymeric material during the manufacture of the core, for example glycerin, triethyl citrate, diethyl phthalate, diethyl sebacate, and the like. The amount of plasticiser added is approximately from 0.01 to 20% by weight, based on the total amount of the therapeutic system.

It is also possible to add surface-active substances, so-called surfactants, in the manufacture of the core, for example anionic surfactants of the alkyl sulphate type, for example sodium, potassium or magnesium n-dodecyl sulphate, n-tetradecyl sulphate, n-hexadecyl sulphate or n-octadecyl sulphate, alkyl ether sulphates, for example sodium, potassium or magnesium n-dodecyloxyethyl sulphate, n-tetradecyloxyethyl sulphate, n-hexadecyloxyethyl sulphate or n-octadecyloxyethyl sulphate or alkanesulphonates, for example sodium, potassium or magnesium n-dodecanesulphonate, n-tetradecanesulphonate, n-hexadecanesulphonate or n-octadecanesulphonate.

Suitable surfactants are, in addition, non-ionic surfactants of the fatty acid/polyhydroxy alcohol ester type, such as sorbitan monolaurate, oleate, stearate or palmitate, sorbitan tristearate or trioleate, polyoxyethylene adducts of fatty acid/polyhydroxy alcohol esters, such as polyoxyethylene sorbitan monolaurate, oleate, stearate, palmitate, tristearate or trioleate, polyethylene glycol/fatty acid esters, such as polyoxyethyl stearate, polyethylene glycol-400 stearate, polyethylene glycol-2000 stearate, especially ethylene oxide/propylene oxide block polymers of the Pluronic ® (BWC) or Synperonic ® (ICI) type.

Further adjuncts are, for example, pulverulent carrier materials, such as lactose, saccharose, sorbitol, mannitol, starch, for example potato starch, corn starch or amylopectin, or cellulose, especially microcrystalline cellulose.

The expression "passage through the casing (a) for the transport of the constituents contained in the core into the surrounding aqueous body fluid" covers apparatus as well as methods suitable for releasing the active ingredient preparation from the core of the therapeutic system. The expression includes passages, openings, bores, holes and the like through the casing (a), acting as a semi-permeable membrane, which connect the surface of the casing and the core. The passage can be made by mechanical drilling or laser drilling or by decomposing a degradable constituent, for example a gelatin plug, forming a passage in the casing of the therapeutic system. In one embodiment the passage can be formed in response to the hydrostatic pressure acting on the therapeutic system. In another embodiment two or more passages can be made at any desired point in the system. The passage can also be formed by mechanical breaking up of the layers during administration of the system. The passage has a minimal diameter which is dependent on the particle size of the crystals of active ingredient. The diameter of the passage must be greater than the average length of the crystals of active ingredient. The maximum diameter is likewise fixed approximately. It should not be so large that it allows aqueous body fluid to enter the therapeutic system as a result of convection. A precise description of the manufacture of the passage and the maximum and minimum dimensions thereof is contained in U.S. Pat. Nos. 3,485,770 and 3,916,899 and the associated drawings.

The therapeutic system according to the invention can be of different shapes and can be, for example, round, oval, oblong or cylindrical or the like, and can be of various sizes depending on the amount it contains. The therapeutic system can, furthermore, be transparent, colourless or coloured and may carry writing to impart an individual appearance to the product and/or to make it instantly recognisable.

The therapeutic system according to the invention has valuable pharmacological properties and can be used in the peroral administration of sparingly soluble active ingredients. An improvement in the therapeutic effect as compared with that of solid forms of administration customary hitherto, such as tablets and dragées, is achieved.

The present invention relates especially to a therapeutic system consisting of
 (a) a casing made of acylated cellulose, for example cellulose acetate, that is permeable to water and impermeable to the components of the core containing the active ingredient and to the ions contained in body fluids, for example in gastric or intestinal juices;
 (b) a core containing an active ingredient that is sparingly soluble in water or a mixture of such active ingredients, a 1:1 mixture (by weight) of vinyl-pyrrolidone/vinyl acetate copolymer with ethylene oxide homopolymer, sodium or potassium chloride for inducing osmosis and optionally further pharmaceutically acceptable adjuncts and
 (c) a passage through the casing (a) for the transport of the constituents contained in the core into the surrounding aqueous body fluid.

The invention relates especially to a therapeutic system consisting of
 (a) a casing made of acylated cellulose, for example cellulose acetate, that is permeable to water and impermeable to the components of the core containing the active ingredient and to the ions contained in body fluids, for example in gastric or intestinal juices;
 (b) a core containing an active ingredient that is sparingly soluble in water or a mixture of such active ingredients, a 1:1 mixture (by weight) of vinyl-pyrrolidone/vinyl acetate copolymer having a molecular weight of $60,000 \pm 15,000$ and a monomer ratio of approximately 60:40 (% by weight) and ethylene oxide homopolymer having a degree of polymerisation of from 2,000 to 100,000 and
 (c) a passage through the casing (a) for the transport of the constituents contained in the core into the surrounding aqueous body fluid.

The present invention relates especially to a therapeutic system for the peroral administration of sparingly soluble active ingredients having the compositions indicated in the Examples.

The therapeutic system according to the invention is manufactured in accordance with processes known per se, for example by comminuting the constituents of the core, mixing them with one another, granulating them and compressing them, covering the core with a casing and, where appropriate, making the passage through the casing (a) for the transport of the constituents contained in the core, for example an opening through the semi-permeable membrane. In the case of active ingredients that form hydrates, the hydrate crystals or, where possible, an anhydrous form of crystal, are comminuted to a mean particle size of approximately 5 $\mu$m. These particles, especially microcrystals, are mixed with the constituents forming the core of the form of administration and granulated, for example by mixing the adjuncts, such as, for example, protective colloids, such as methylhydroxypropylcellulose or methyl cellulose, sodium chloride and Polyox ® with the active ingredient and adding to this mixture a solution of polyvinylpyrrolidone/polyvinyl acetate in an organic solvent or water, removing the solvent and granulating and drying the residue. The granulate is then compressed and punched out into shapes, for example tablet cores, optionally with the addition of glidants, for example magnesium stearate, of conventional shape and size; for example, approximately 5–12 mm in diameter (round shapes) and approximately 4–8 mm (in width) and approximately 10–22 mm (in length-oblong shapes).

All solvents in which copolymers of polyvinylpyrrolidone and polyvinyl acetate are soluble, especially water or lower alkanols, such as methanol, ethanol or isopropanol, are suitable.

The semi-permeable casing can be applied to the core containing the active ingredient by pouring, moulding, spraying or by dipping the capsule into the material forming the semi-permeable casing. Another process that can be used to apply the casing is the air suspension procedure. This process comprises suspending and tumbling the materials (capsules or capsule cores) in a stream of air and an agent forming the casing until the casing surrounds and covers the core. The air suspension procedure is described in U.S. Pat. No. 2,799,241 and in J. Am. Pharm. Assoc., Vol. 48, p. 451–459, 1979, and in Volume 49, p. 82 to 84, 1980. An example of other preferred standard processes is the spray pan process which is described in Remington's Pharmaceutical Sciences, 14th Edition, on pages 1686–1687.

The passage in the semi-permeable casing can be produced subsequently by mechanical drilling or using a laser. The following Examples illustrate the invention.

Example 1:
Therapeutic system for carbamazepine (TEGRETOL ® - 200 mg)

| Core | |
|---|---|
| carbamazepine - anhydrous (Tegretol ®) | 200 mg |
| microcrystalline cellulose (Avicel ®) | 20 mg |
| methylhydroxypropylcellulose (Pharmacoat ®603) | 12.5 mg |
| vinylpyrrolidone/vinyl acetate-60:40-copolymer (Kollidon ® VA 64) | 80 mg |
| polyethylene glycol (MW: 5 × 106-Polyox ®-coagulant) | 80 mg |
| sodium chloride | 80 mg |
| sodium lauryl sulphate | 6 mg |
| magnesium stearate | 10.5 mg |
| | = 500 mg |
| Casing | |
| cellulose acetate 320 | 16 mg |
| cellulose acetate 39.8 | 20 mg |
| polyethylene glycol 4000 | 4 mg |
| | = 40 mg |
| total weight | approx. 540 mg |

Anhydrous carbamazepine, which is ground to an average particle size of 5 μm, methylhydroxypropylcellulose, sodium chloride and sodium lauryl sulphate are mixed in a planet mixer. This mixture is granulated with some of the vinylpyrrolidone/vinyl acetate copolymer dissolved in a methanol/isopropanol mixture. The mixture is forced through a sieve, and the resulting granules are dried in vacuo.

The dry granulate is mixed with the remainder of the vinylpyrrolidone/vinyl acetate copolymer, Avicel ® and magnesium stearate. The homogeneous mixture is then compressed and punched out (punch size 10 mm diameter).

The resulting tablet cores are coated in a fluidised bed coater (Aeromatic Strea ® 1) with an organic lacquer containing the constituents of the casing of the therapeutic system. The coated tablets are dried in a drying oven at 40° C. for 48 hours. An opening 750 μm in diameter is made in each tablet using a drill or a laser.

Example 2:
Therapeutic system for acetylsalicylic acid

| Core | |
|---|---|
| acetylsalicylic acid | 500 mg |
| microcrystalline cellulose (Avicel ®) | 40 mg |
| Kollidon ® VA 64 | 160 mg |
| polyethylene glycol (MW: 5 × 106-Polyox ®-coagulant) | 80 mg |
| sodium chloride | 120 mg |
| magnesium stearate | 20 mg |
| | = 1000 mg |
| Casing | |
| cellulose acetate 320 | 20 mg |
| cellulose acetate 39.8 | 30 mg |
| polyethylene glycol 4000 | 6 mg |
| | = 56 mg |
| total weight | approx. 1056 mg |

The manufacture of the form of administration is effected analogously to Example 1 (punch size 21×9 mm) using acetyl-salicylic acid (dried) ground dry to an average particle size of approximately from 5.0 to 10.0 μm.

Example 3:
Therapeutic system for theophylline

| Core | |
|---|---|
| theophylline | 200 mg |
| microcrystalline cellulose (Avicel ®) | 20 mg |
| Kollidon ® VA 64 | 80 mg |
| polyethylene glycol (MW: 5 × 106-Polyox ®-coagulant) | 80 mg |
| magnesium stearate | 10 mg |
| | 500 mg |
| Casing | |
| cellulose acetate 320 | 23 mg |
| cellulose acetate 39.8 | 10 mg |
| polyethylene glycol 4000 | 4 mg |
| | = 37 mg |
| total weight | approx. 537 mg |

The manufacture of the form of administration is effected analogously to Example 1 (punch size 10.5 mm diameter) using theophylline (dried) ground dry to an average particle size of approximately from 5.0 to 10.0 μm.

Example 4:
Therapeutic system for nifedipine

| Core | |
|---|---|
| nifedipine | 50.0 mg |
| Kollidon ® VA 64 | 18.0 mg |
| polyethylene glycol (MW: 5 × 106-Polyox ®-coagulant) | 20.0 mg |
| sodium chloride | 20.0 mg |
| magnesium stearate | 2.0 mg |
| | = 110.0 mg |
| Casing | |
| cellulose acetate 320 | 15.0 mg |
| polyethylene glycol 4000 | 2.0 mg |
| | = 17.0 mg |
| total weight | approx. 127.0 mg |

The manufacture of the form of administration is effected analogously to Example 1 (punch size 7 mm diameter) using nifedipine (dried) ground dry to an average particle size of approximately from 5.0 to 10.0 μm.

I claim:

1. Peroral therapeutic system in tablet form for continuous and controlled administration of active ingredients that are sparingly soluble in water, consisting of
   (a) a casing made of a material that is permeable to water and impermeable to the components of the core containing the active ingredient,
   (b) a compressed core from a granular powder of an active ingredient that is sparingly soluble in water or a mixture of such active ingredients, a hydrophilic, polymeric swelling agent consisting of a mixture of a vinylpyrrolidone/vinyl acetate copolymer with an ethylene oxide homopolymer, optionally a water-soluble substance for inducing osmosis and optionally other pharmaceutically acceptable adjuncts and
   (c) a passage through the casing (a) for the transport of the constituents contained in the core into the surrounding aqueous body fluid.

2. Peroral therapeutic system in tablet form according to claim 1, consisting of (a) a casing made of acylated cellulose, that is permeable to water and impermeable to the components of the core containing the active ingredient and to the ions contained in body fluids,
(b) a compressed core from a granular powder of an active ingredient that is sparingly soluble in water or a mixture of such active ingredients, a 1:1 mixture (by weight) of a vinyl-pyrrolidone/vinyl acetate copolymer with an ethylene oxide homopolymer, sodium or potassium chloride for inducing osmosis and optionally other pharmaceutically acceptable adjuncts and
(c) a passage through the casing (a) for the transport of the constituents contained in the core into the surrounding aqueous body fluid.

3. Peroral therapeutic system in tablet form according to claim 1, consisting of
(a) a casing made of acylated cellulose, that is permeable to water and impermeable to the components of the core containing the active ingredient and to the ions contained in body fluids,
(b) a compressed core from a granular powder of an active ingredient that is sparingly soluble in water or a mixture of such active ingredients, a 1:1 mixture (by weight) of a vinyl-pyrrolidone/vinyl acetate copolymer having a molecular weight of $60,000 \pm 15,000$ and a monomer ratio of approximately 60:40 (% by weight) and an ethylene oxide homopolymer having a degree of polymerisation of from 2,000 to 100,000 and
(c) a passage through the casing (a) for the transport of the constituents contained in the core into the surrounding aqueous body fluid.

4. Peroral therapeutic system in tablet form according to claim 2 wherein said acylated cellulose is cellulose acetate.

5. Peroral therapeutic system in tablet form according to claim 2 wherein said body fluids are gastric or intestinal juices.

6. Peroral therapeutic system in tablet form according to claim 3 wherein said acylated cellulose is cellulose acetate.

7. Peroral therapeutic system in tablet form according to claim 3 wherein said body fluids are gastric or intestinal juices.

* * * * *